United States Patent
Myllyoja et al.

(10) Patent No.: US 9,914,690 B2
(45) Date of Patent: Mar. 13, 2018

(54) METHOD FOR CATALYTIC CONVERSION OF KETOACIDS VIA KETOACID DIMER INTERMEDIATE AND HYDROTREATMENT TO HYDROCARBONS

(71) Applicant: NESTE OYJ, Espoo (FI)

(72) Inventors: Jukka Myllyoja, Vantaa (FI); Rami Piilola, Helsinki (FI); Maaria Seläntaus, Helsinki (FI); Mats Käldström, Porvoo (FI); Marina Lindblad, Helsinki (FI); Elias Ikonen, Espoo (FI)

(73) Assignee: NESTE OYJ, Espoo (FI)

( * ) Notice: Subject to any disclaimer, the term of this patent is extended or adjusted under 35 U.S.C. 154(b) by 11 days.

(21) Appl. No.: 15/010,972

(22) Filed: Jan. 29, 2016

(65) Prior Publication Data
US 2016/0221912 A1   Aug. 4, 2016

(30) Foreign Application Priority Data
Jan. 30, 2015   (EP) .................................. 15153265

(51) Int. Cl.
*C07C 51/353* (2006.01)
*C01G 3/00* (2006.01)
*C10M 105/00* (2006.01)
*C07C 51/367* (2006.01)
*C10G 45/58* (2006.01)
*C10G 65/04* (2006.01)
*C10G 3/00* (2006.01)

(52) U.S. Cl.
CPC .......... *C07C 51/353* (2013.01); *C07C 51/367* (2013.01); *C10G 3/50* (2013.01); *C10G 45/58* (2013.01); *C10G 65/043* (2013.01); *C10M 105/00* (2013.01); *C10L 2200/0469* (2013.01); *Y02P 30/20* (2015.11)

(58) Field of Classification Search
CPC ....... C07C 51/353; C07C 51/367; C10G 3/50; C10G 45/58; C10G 65/043; C10M 105/00
See application file for complete search history.

(56) References Cited

U.S. PATENT DOCUMENTS

| | | | | |
|---|---|---|---|---|
| 3,195,992 A | * | 7/1965 | Barusch | .................... C10L 1/06 44/454 |
| 2006/0135793 A1 | * | 6/2006 | Blessing | ................ C07C 69/716 549/318 |
| 2012/0203043 A1 | | 8/2012 | Wheeler et al. | |

FOREIGN PATENT DOCUMENTS

RU    2182163 C2    5/2002
WO    2006/056591 A1    6/2006

OTHER PUBLICATIONS

European Search Report dated Jul. 10, 2015, by the European Patent Office in corresponding European Application No. 15153265. (2 pages).
Serrano-Ruiz et al., "Conversion of cellulose to hydrocarbon fuels by progressive removal of oxygen," Applied Catalysis B: Environmental, (Oct. 11, 2010), vol. 100, No. 1-2, pp. 184-189.
Mascal et al., "Hydrodeoxygenation of the Angelica Lactone Dimer, a Cellulose-Based Feedstock: Simple, High-Yield Synthesis of Branched C7-C10 Gasoline-like Hydrocarbons", Angewandte Chemie, 2014, 126, pp. 1885-1888.
Amarasekara et al., "NaOH catalyzed condensation reactions between levulinic acid and biomass derived furan-aldehydes in water," Industrial Crops and Products, 65, 2015, pp. 546-549 (4 pages).
Search report issued by the Russian Patent Office in the corresponding Russian Patent Application dated May 30, 2017 (10 pages).

* cited by examiner

*Primary Examiner* — Pancham Bakshi
*Assistant Examiner* — Mark R Luderer
(74) *Attorney, Agent, or Firm* — Buchanan Ingersoll & Rooney PC (57) ABSTRACT

The present invention relates to catalytic conversion of ketoacids, including methods for increasing the molecular weight of ketoacids. The method can include providing in a reactor a raw material having at least one ketoacid. The raw material is then subjected to one or more C—C-coupling reaction(s) in the presence of an ion exchange resin catalyst to produce at least one ketocid dimer. The method can include providing in a reactor a feedstock having the at least one ketoacid dimer and subjecting the feedstock to one or more C—C-coupling reaction(s) at a temperature of at least 200° C.

25 Claims, 3 Drawing Sheets

Figure 1 – Conversion of lignocellulosic material to levulinic acid

Figure 2 – Reaction products of levulinic acid dimers

Figure 3 – Process scheme for upgrading second C-C coupling reaction products

Figure 4 – Process scheme

METHOD FOR CATALYTIC CONVERSION OF KETOACIDS VIA KETOACID DIMER INTERMEDIATE AND HYDROTREATMENT TO HYDROCARBONS

TECHNICAL FIELD

The present invention relates to catalytic conversion of ketoacids, including methods for increasing the molecular weight of ketoacids, products obtainable by such methods, as well as use of such products for the production of liquid hydrocarbons and/or gasoline or diesel fuel or base oil components.

BACKGROUND ART

Production of hydrocarbons used as fuel or base oil components and chemicals from biomass are of increasing interests since they are produced from a sustainable source of organic compounds.

Figure 1:
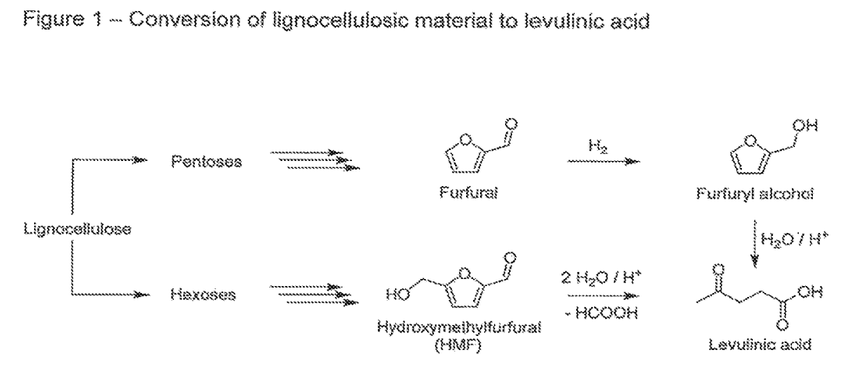
FIG. 1 shows a scheme illustrating conversion of lignocellulosic material to levulinic acid.

The ketoacid Levulinic Acid (LA, 4-oxopentanoic acid) is one of many platform molecules that may be derived from biomass. It may be produced from both pentoses and hexoses of lignocellulosic material (see FIG. 1) at relatively low cost. Some of the advantages and drawbacks of using levulinic acid as a platform molecule relates to the fact that it is considered to be a reactive molecule due to both its keto and acid functionality.

Esters of levulinic acid have been suggested as fuel components as well as cold flow additives in diesel fuels, and in particular the methyl and ethyl esters have been used as additives in diesel fuel. Gamma-valerolactone (GVL), which may be obtained by reduction of levulinic acid, has been used as a fuel additive in gasoline. Further reduction of GVL to 2-methyltetrahydrofuran (MTHF) provides a product that may be blended with gasoline of up to 60%. Alkyl valerates produced from levulinic acid have also been suggested as biofuels.

Levulinic acid has also been used for the production of liquid hydrocarbon fuels by a number of catalytic routes, including a method of producing a distribution of alkenes, the distribution centered around $C_{12}$, involving converting aqueous GVL in a first reactor system to butenes followed by oligomerization in a second reactor over an acidic catalyst (e.g. Amberlyst® 70).

Serrano-Ruiz et al. (*Appl. Catal., B*, 2010, 100, 184) produced a $C_9$-ketone (5-nonanone) by reducing levulinic acid to GVL over a Ru/C catalyst in one reactor followed by reacting 40 wt % GVL in water and 0.02 M $H_2SO_4$ in a Pd/$Nb_2O_5$+ceria-zirconia double bed arrangement at 325-425° C., 14 bar, WHSV=0.8-0.5 $h^{-1}$ in another reactor.

US 2006/0135793 A1 (to Blessing and Petrus) disclose dimerization of levulinic acid to a $C_{10}$ unit in the presence of hydrogen, with a strong acidic heterogenous catalyst, e.g. ion exchange resin catalyst.

SUMMARY OF INVENTION

Upgrading levulinic acid and other ketoacids to higher molecular weight compounds can be achieved through reaction routes involving single or multiple reaction steps, both of which have certain advantages and disadvantages. Using a single reactor compared to multiple reactors may be advantageous in that they reduce the number of process steps and therefore improve process economy. Some of the drawbacks associated with direct routes of upgrading e.g. by using single reactors are that these reactions generate highly reactive intermediates with more than one functional group, which can further react to other undesired molecules resulting in catalyst deactivation. Suppression of side reactions usually also entails a lower yield of the desired products due to use of lower temperatures, dilute solutions of reactants or less reactive catalysts. Accordingly, an indirect route of upgrading a raw material using multiple reactors or multiple catalyst beds in a single reactor may in some situations be preferred compared to a direct route of upgrading.

Consequently, there is a need for additional processes for upgrading levulinic acid and other ketoacids to higher molecular weight compounds, which are suitable for use as e.g. fuel or base oil components or chemicals or as components in the production of fuel or base oil components or chemicals. In particular, there is a need for such additional processes, which reduce the processing costs by i.a. improving the yield of the desired components or chemicals and/or reduce the overall catalyst consumption by improving the life time of the catalyst.

The present invention was made in view of the prior art described above, and one of the objects of the present invention is to provide methods that enable upgrading of ketoacids via improved routes to higher molecular weight compounds.

Another object of the present invention is to provide the upgrade of ketoacids to higher molecular weight compounds in good yield and at low processing costs.

The inventors of the present invention have found that the challenges related to formation of reactive intermediates and catalyst deactivation can be alleviated by selective conversion of ketoacids to ketoacid dimers in the presence of an ion exchange resin catalyst and subsequent conversion of the ketoacid dimers via C—C-coupling reactions to higher molecular weight compounds at temperatures of 200° C. or above.

It has also been found that ketoacid dimers obtained by C—C-coupling reactions in the presence of an ion exchange resin (IER) catalyst are especially suitable for conversion to higher molecular weight compounds through C—C-coupling reactions. Without being bound to any theory, it is considered that the IER catalyst catalyses aldol condensation reactions of levulinic acid producing levulinic acid dimers comprising two carboxylic acid groups. The presence of carboxylic acid groups in the levulinic acid dimers obtained with IER catalyst makes them highly reactive at temperatures of above 200° C.

The higher molecular weight components produced with the method of the invention are suitable for use as e.g. fuel or base oil components or chemicals or as components in the production of fuel or base oil components or chemicals.

Thus the present invention provides a method for increasing the molecular weight of a ketoacid as defined in claim 1.

In the step of subjecting the feedstock to second C—C-coupling reaction(s), the at least one ketoacid dimer undergoes at least one C—C-coupling reaction with another ketoacid dimer, ketoacid dimer derivative, ketoacid or ketoacid derivative present in the feedstock so as to increase the molecular weight of the ketoacid dimer. The ketoacid dimers participating in the C—C-coupling reaction may be of the same type (having the same chemical formula) or of a different type. The ketoacid dimer derivative includes all compounds directly obtainable from ketoacid dimer through C—C-coupling reactions or other reactions such as lactonisation and dehydroxylation. Examples of ketoacid dimers according to the invention are shown by the following formulas, using levulinic acid dimers as examples:

Examples of ketoacid dimer derivatives according to the invention are shown by the following formulas, using levulinic acid dimers as examples:

The ketoacid derivate includes all compounds directly obtainable from a ketoacid through C—C-coupling reactions or lactonisation and dihydroxylation reactions. The ketoacid derivatives may be selected from the list consisting of lactones and lactone derivatives of ketoacids, and pentanoic acid.

In the second C—C-coupling reaction(s) the at least one ketoacid dimer reacts with another reactant with the formation of a new carbon-carbon bond in the product. In other words, the molecular weight of the ketoacid dimer is increased using the ketoacid dimer as a direct precursor (one-step reaction) and within a single reactor or a single catalyst bed. As a matter of course, further C—C-coupling reactions may occur so as to further increase the molecular weight the C—C-coupling reaction product. Preferably, these further reactions are conducted in the same (single) reactor or catalyst bed.

The at least one ketoacid dimer is preferably a dimer of γ-ketoacid, most preferably levulinic acid dimer. The at least one ketoacid dimer may be a mixture of different ketoacid dimers.

Preferably, the first and second C—C-coupling reaction(s) are conducted in a first and in a second reactor, respectively. In this respect, it is to be noted that the term "a reactor" in the present invention refers to a reactor vessel, which may comprise one or more catalyst beds or to a single catalyst bed inside reactor vessel comprising one or more catalyst beds.

Accordingly, the method of the present invention is two-step method in which first a ketoacid dimer is produced and then the produced ketoacid dimer is further subjected to the second C—C-coupling reaction. The two-steps of the present invention are not conducted in a one-pot reaction, i.e. not in the same reaction liquid at the same time. Rather the reactions are separated in space and/or time, i.e. spatially and/or chronologically. That is, the two-step reaction does not encompass the intermediate (temporary) production of ketoacid dimers which are immediately further subjected to the second C—C-coupling reaction, but the first C—C-coupling reaction is carried out, then the reaction conditions are changed (e.g. by increasing the temperature of the reaction liquid and/or by bringing the reaction liquid to a different reactor or to a different part of a flow reactor) and then the second C—C-coupling reaction is carried out.

The first and second reactor employed in the method of the present invention may be a flow reactor, preferably a continuous flow reactor. Alternatively, the first and/or the second reactor may be a batch reactor, preferably under stirring. A flow reactor type is preferred from the viewpoint of production efficiency. Most preferably the second C—C-coupling reaction is conducted downstream the first C—C-coupling reaction. When using a flow reactor, the catalyst system is preferably immobilized in the reactor.

The second C—C-coupling reaction(s) are preferably conducted in strong solutions of ketoacid dimers in the feedstock. Preferably the content of the at least one ketoacid dimer in the feedstock is at least 30 wt-%, preferably at least 40 wt-%, more preferably at least 50 wt-%, even more preferably at least 55 wt-%, and even more preferably at least 60 wt-%. If multiple ketoacid dimers are present in the feedstock, the "content of the at least one ketoacid dimer" refers to the total content of all ketoacid dimers.

In this respect, it is to be noted that the term "feedstock" in the present invention includes all material fed to the reactor, except for the material constituting the catalyst system, if present. Thus, the calculation of the content of the at least one ketoacid dimer in the feedstock does not consider the amount of catalyst if the reaction is conducted in the presence of a catalyst.

Using strong solutions of ketoacid dimers allows for high probability of C—C-coupling reactions between two ketoacid dimers, thus providing a high yield of desired products and low amounts of side-products. The solvent of the (strong) solution may be any ketoacid or ketoacid dimer. In addition, water and/or organic solvents may be used.

The content of water in the feedstock is preferably less than 10.0 wt-%, and more preferably less than 5.0 wt-% and even more preferably less than 2.0 wt-%. The calculation of the content of water in the feedstock does not consider the amount of catalyst, if present. The first C—C-coupling reaction(s) of ketoacids in the presence of the ion exchange resin catalyst are known to proceed at least to some extent through aldol condensation reactions, in which water is formed. The water formed during the first C—C-coupling reactions in the first reactor may be at least partially removed before providing the feedstock in the second reactor.

In the step of subjecting the raw material to first C—C-coupling reaction(s), the at least one ketoacid undergoes at least one C—C-coupling reaction with another ketoacid or ketoacid derivative present in the raw material so as to produce a ketoacid dimer. The ketoacids participating in the C—C-coupling reaction may be of the same type having the same chemical formula or of a different type.

In the first C—C-coupling reaction the at least one ketoacid reacts with another ketoacid or ketoacid derivative under the formation of a new carbon-carbon bond in the product. In other words, the molecular weight of the ketoacid is increased using the ketoacid as a direct precursor (one-step reaction) and within a single reactor or a single catalyst bed.

Preferably the at least one ketoacid in the raw material is a γ-ketoacid, preferably levulinic acid.

Preferably the average pore diameter of the ion exchange resin catalyst in the range of 150 Å-300 Å, preferably 200-250 Å. The average pore size diameter of the ion exchange resin catalyst can be measured with BET-method, which measures the adsorption isotherm of nitrogen (ASTM D-3663-03(2008)).

The specific surface is generally determined by the BET method, which measures the adsorption isotherm of nitrogen (ASTM D-3663-03(2008)).

Preferably the raw material is subjected to the first C—C-coupling reaction(s) at a temperature of 100-190° C., preferably 120-160° C., more preferably 120-140° C.

This temperature range was found to be particularly suitable for obtaining a high yield of ketoacid dimers suitable to be used as the at least one ketoacid dimer in the next step of the method.

It has also been found that the stability of the ion exchange catalyst and the yield of dimers can be improved if the raw material is subjected to C—C-coupling reactions in the presence of hydrogen and if the ion exchange resin catalyst comprises a hydrogenating metal. Preferably the hydrogenating metal is selected from the group consisting of Ni, Mo, Co, Ru, Rh, Pd, Pt, or a combination of these.

The feedstock may be subjected to second C—C-coupling reactions in the presence of a catalyst or without a catalyst, in which case the second C—C-coupling reactions proceed through thermal reactions. Thermal reactions are favourable from an economic point of view since conducting the C—C-coupling reactions without a catalyst decreases the process costs and increases the economic viability of the process.

The inventors have also found that the feedstock may be subjected to the second C—C-coupling reactions in the presence of a solid metal oxide catalyst system, which preferably comprises a first metal oxide and a second metal oxide. The catalyst system comprising a first metal oxide and a second metal oxide is suited to catalyse multiple types of C—C-coupling reactions of ketoacid dimers enabling the production of higher molecular weight compounds of ketoacids at a good yield and in a single reactor.

The choice between catalytic and non-catalytic second C—C-coupling reaction depends on the type of desired product compounds. Thermal reactions of ketoacid dimers have been found to produce a wide variety of C—C-coupling reaction products which are suitable for use as fuel components, base oil components and chemicals. Catalytic C—C-coupling reactions of ketoacid dimers have been found to produce somewhat narrower distribution of products, which are also suitable for use as fuel components, base oil components and chemicals.

Preferably, the solid metal oxide catalyst system comprises a mixture of the first metal oxide and second metal oxide.

The catalyst system has preferably a specific surface area of from 10 to 500 $m^2/g$. The specific surface is generally determined by the BET method, which measures the adsorption isotherm of nitrogen (ASTM D-3663).

In the present invention, the mixture of metal oxides includes a mixture of individual metal oxide materials, e.g. in a powder form, mixed metal oxides, where the metal oxides form a common matrix, and supported metal oxides, where the more active metal oxide is deposited on the metal oxide acting as a carrier.

Various methods can be used for the preparation of mixtures of metal oxides. In preparation of mixed metal oxides, metal oxide precursors may be brought together from gas phase or liquid solution before transformation into oxide form. In preparation of supported metal oxides, a metal oxide precursor may be brought from gas phase or liquid solution onto a solid support in oxide (or hydroxide) form before the transformation of the metal oxide precursor into oxide form.

Preferably, the solid metal oxide catalyst system comprises a first metal oxide supported on a second metal oxide as carrier.

Preferably the surface density of metal atoms of the first metal oxide supported on the second metal oxide is from 0.5 to 20 metal atoms/$nm^2$. The surface density of metal atoms of the first metal oxide in the catalyst system is calculated based on the content of metal oxide in the catalyst and specific surface area of the catalyst system. E.g. $K_2O/TiO_2$ catalyst used in the invention has a $K_2O$ content of 2.4 wt-% and the catalyst has a specific surface of X $[m^2/g]$, thus the K atom density is $(2*0.024 [g/g]/94.2 [g/mol])*6.022*10^{23}$ $[atoms/mol]/X [m^2/g]*10^{18} [nm^2/m^2]$ (if $X=100$ $m^2/g$)=3.06 atoms/$nm^2$.

There are several metal oxides, which can be used in the catalyst system to catalyse the C—C-coupling reactions of ketoacid dimers. Preferably the first metal oxide comprises an oxide of one of K, Li, Be B, Na, Mg, Al, Si, Ca, Sc, Ti, V, Cr, Mn, Fe, Co, Ni, Cu, Zn, Br, Sr, Y, Zr, Nb, Mo, Ba, W, Pb, Bi, La, Ce, Th, and the second metal oxide comprises an oxide of one of K, Li, Be B, Na, Mg, Al, Si, Ca, Sc, Ti, V, Cr, Mn, Fe, Co, Ni, Cu, Zn, Br, Sr, Y, Zr, Nb, Mo, Ba, W, Pb, Bi, La, Ce, Th or a combination of these, the first metal oxide not being same as second metal oxide.

Preferably the first metal oxide comprises an oxide of one of K, Li, Be B, Na, Mg, Al, Si, Ca, Sr, and Ba and the second metal oxide comprises an oxide of one of Ti, Sc, V, Cr, Mn, Fe, Co, Ni, Cu, Zn, Br, Sr, Y, Zr, Nb, Mo, Ba, W, Pb, Bi, La, Ce, Th, or a combination of these.

Preferably, the catalyst system comprises potassium oxide as the first metal oxide and titanium oxide as the second metal oxide.

Preferably the content of the first metal oxide in the catalyst system is 1.0 to 40.0 wt-%, preferably 2.0 to 30.0 wt-%, further preferably 13.0 to 30.0 wt-%, calculated by weight of the metal oxide in relation to the total mass of the catalyst. The metal oxide content is determined by measuring the metal content in the catalyst and calculating the content of the metal oxide in which the metal is present in the highest oxidation number, if multiple (stable) oxides of one metal exist.

Preferably the feedstock further comprises at least one ketoacid, preferably a γ-ketoacid, more preferably levulinic acid.

It has been found that the reactivity of the ketoacid dimers in thermal or catalytic C—C-coupling reactions is enhanced by addition of more reactive forms of ketoacids (i.e. monomers) to the feedstock. Preferably the content of the at least one ketoacid in the feedstock is at least 1.0 wt-%, preferably at least 5.0 wt-%, more preferably at least 10.0 wt-%, or at least 20.0 wt-%. If multiple types of ketoacids are present in the feedstock, the "content of the at least one ketoacid" refers to the total content of all ketoacids (excluding the ketoacid dimers and other ketoacid oligomers).

Preferably the weight ratio of the at least one ketoacid content to the at least one ketoacid dimer content in the feedstock is in the range of 1:5 to 10:1, preferably 1:3 to 5:1.

Preferably the feedstock is introduced into the reactor in liquid phase, as opposed to for example the gaseous phase. One of the advantages of introducing the feedstock into the reactor in the liquid phase is that it is not required to heat the product to prepare a gaseous stream. Further, the presence of solid components in the feedstock may lead to clogging of the catalyst. Therefore, it is preferred that the feedstock is in liquid phase and does not include a considerable amount of solid material, e.g. less than 4.0 wt-%, preferably less than 1.0 wt-%, more preferably less than 0.2 wt-% of solid material. Here, solid material includes solid material suspended or dispersed in a liquid phase.

The C—C-coupling reaction(s) can be controlled by adjusting several parameters, including by selection of reaction conditions such as: temperature, pressure, and weight hourly space velocity (WHSV) (kg feedstock or raw material/kg catalyst per hour).

Preferably, the second C—C-coupling reaction(s) are conducted at a temperature which is at least 10° C., more preferably at least 20° C., further preferably at least 40° C. higher than the temperature employed in the first C—C-coupling reaction.

The second C—C-coupling reaction(s) for increasing the molecular weight of ketoacid dimers are preferably conducted at a temperature of 200-400° C., preferably 210-300° C., more preferably 220-280° C. and even more preferably 220-260° C. This temperature range was found to be particularly suitable for obtaining a high degree of reaction products comprising more than two ketoacid units (C13-C30) while avoiding excessive polymerization and coking of the catalyst.

Preferably the second C—C-coupling reaction(s) are conducted at a pressure of 0.5-100 bar, preferably 1.0-50 bar, more preferably 1.0-20 bar.

The second C—C-coupling reactions, when employing a catalyst, are preferably conducted at a weight hourly space velocity of 0.05 $h^{-1}$ to 2.0 $h^{-1}$, preferably 0.1 $h^{-1}$ to 1.8 $h^{-1}$, more preferably 0.2 $h^{-1}$ to 1.5 $h^{-1}$, most preferably 0.25 $h^{-1}$ to 1.25 $h^{-1}$. The WHSV has an influence on the composition of the resulting material, since it determines the effective contact time of reagent and catalyst. The above-mentioned ranges have shown to provide a high degree of favourable products.

The second C—C-coupling reaction(s) may be conducted in the presence of hydrogen. In this case, the hydrogen is fed to the reactor as part of the feedstock. It is also possible to conduct the second C—C-coupling reaction(s) in the absence of hydrogen and to recover the catalyst by adding hydrogen to the reaction mixture from time to time.

The second C—C-coupling reactions may be conducted at a feed ratio (H2/liquid feedstock) of 100-3000 Nl/l, preferably 200-2000 Nl/l, more preferably 500-1800 Nl/l and most preferably 500-1500 Nl/l. Here the liquid feedstock refers to feedstock, which is predominantly in liquid form at the reaction conditions.

If the C—C-coupling reaction(s) are conducted in the presence of hydrogen, the metal oxide catalyst system may also comprise at least one hydrogenation metal selected from Group VIII of the Periodic Table of Elements, preferably Co, Ni, Ru, Rh, Pd, and Pt.

The second C—C-coupling reaction(s) may be conducted under a flow of nitrogen. The nitrogen flow has been found to strip water and CO2 formed in the reactions thus improving the product yield. Preferably, the feed ratio of nitrogen (N2/liquid feedstock) is 100-3000 Nl/l, preferably 200-2000 Nl/l, more preferably 500-1800 Nl/l and most preferably 500-1500 Nl/l. The combined use of hydrogen and nitrogen showed particularly favourable results.

The characteristics of dimers in the feedstock depend on the method used to produce the dimers. Preferably the at least one ketoacid dimer is selected from a group of 4-hydroxy-4-methyl-6-oxononanedioic acid, 3-acetyl-4-hydroxy-4-methylheptanedioic acid, 5-(2-methyl-5-oxotetrahydrofuran-2-yl)-4-oxopentanoic acid, (E)-4-methyl-6-oxonon-4-enedioic acid, 4-hydroxy-6-methylnonanedioic acid, (E)-6-hydroxy-4-methylnon-4-enedioic acid, (Z)-3-acetyl-4-methylhept-3-enedioic acid, 3-(3-acetyl-2-methyl-5-oxotetrahydrofuran-2-yl)propanoic acid, (Z)-3-1(1-hydroxyethyl)-4-methylhept-3-enedioic acid, 3-(1-hydroxyethyl)-4-methylheptanedioic acid or a combination thereof.

In a further aspect of the present invention, a reaction product of the second C—C-coupling reaction(s) obtainable by the method according to the present invention is provided.

In another aspect of the present invention, a method for producing hydrocarbons from a raw material comprising at least one ketoacid is provided.

In still another aspect of the present invention, a hydrocarbon composition obtainable by the method according to the present invention is provided.

In brief, the present invention relates to one or more of the following items:

1. A method for increasing the molecular weight of a ketoacid, the method comprising the steps of providing in a reactor a raw material comprising at least one ketoacid and subjecting the raw material to first C—C-coupling reaction(s) in the presence of an ion exchange resin catalyst so as to produce at least one ketoacid dimer, providing in a reactor a feedstock comprising the at least one ketoacid dimer, subjecting the feedstock to second C—C-coupling reaction(s) at a temperature of at least 200° C.

2. The method according to item 1, wherein the at least one ketoacid dimer is a dimer of a γ-ketoacid, preferably a dimer of levulinic acid.

3. The method according to item 1 or 2, wherein the first and second C—C-coupling reaction(s) are conducted in first and second reactors, respectively.

4. The method according to any of items 1-3, wherein the content of the at least one ketoacid dimer in the feedstock is at least 30 wt-%, preferably at least 40 wt-%, more preferably at least 50 wt-%, even more preferably at least 55 wt-%, and even more preferably at least 60 wt-%.

5. The method according to any of the items 1-4, wherein the content of water in the feedstock is less than 15.0 wt-%, preferably less than 10.0 wt-%, more preferably less than 5.0 wt-%.

6. The method according to any of items 1-5, wherein the at least one ketoacid in the raw material is γ-ketoacid, preferably levulinic acid.

7. The method according to any of items 1-6, wherein the average pore diameter of the ion exchange resin catalyst in the range of 150-300 Å, preferably 200-250 Å.

8. The method according to any of items 1-7, wherein the first C—C-coupling reaction(s) are conducted at a temperature in the range of 100-190° C., preferably 120-160° C., more preferably 120-140° C.

9. The method according to any of items 1-8, wherein the raw material is subjected to the first C—C-coupling reaction(s) in the presence of hydrogen.

10. The method according to item 9, wherein the ion exchange resin catalyst comprises at least one hydrogenating metal selected from Group VIII of the Periodic Table of Elements, preferably Co, Ni, Ru, Rh, Pd, and Pt, more preferably Pd.

11. The method according to any of items 1-10, wherein the feedstock is subjected to the second C—C-coupling reactions in the absence of a catalyst.

12. The method according to any of items 1-10, wherein the feedstock is subjected to the second C—C-coupling reaction(s) in the presence of a solid metal oxide catalyst system comprising a first metal oxide and the second metal oxide.

13. The method according to item 12, wherein the catalyst system has a specific surface area of from 10 to 500 $m^2/g$.

14. The method according to any of item 12 or 13, wherein in the solid catalyst system comprises a mixture in which the first metal oxide is supported on the second metal oxide.

15. The method according to any of items 12-14, wherein the surface density of metal atoms of the first metal oxide supported on the second metal oxide is from 0.5 to 20 metal atoms/$nm^2$.

16. The method according to any of items 12-15, wherein the first metal oxide comprises an oxide of one of K, Li, Be B, Na, Mg, Al, Si, Ca, Sc, Ti, V, Cr, Mn, Fe, Co, Ni, Cu, Zn, Br, Sr, Y, Zr, Nb, Mo, Ba, W, Pb, Bi, La, Ce, Th and the second metal oxide comprises one of K, Li, Be B, Na, Mg, Al, Si, Ca, Sc, Ti, V, Cr, Mn, Fe, Co, Ni, Cu, Zn, Br, Sr, Y, Zr, Nb, Mo, Ba, W, Pb, Bi, La, Ce, Th, or a combination of these, the first metal oxide not being same as second metal oxide.

17. The method according to any of items 12-16, wherein the first metal oxide comprises an oxide of potassium and the second metal oxide comprises an oxide of titanium.

18. The method according to any of items 12-16, wherein the first metal oxide comprises an oxide of tungsten or cerium and the second metal oxide comprises an oxide of zirconium, titanium, silicon, vanadium, or chromium, preferably an oxide of zirconium or titanium.

19. The method according to any of items 12-18, wherein the content of the first metal oxide in the catalyst system is 1.0 to 40.0 wt %, preferably 2.0 to 30.0 wt-%, further preferably 13.0 to 30.0 wt-% calculated by weight of metal oxide relative to the total mass of the catalyst.

20. The method according to any of items 1-19, wherein the feedstock further comprises at least one ketoacid, preferably a γ-ketoacid, more preferably levulinic acid.

21. The method according to item 20, wherein the content of the at least one ketoacid in the feedstock is at least 1.0 wt-%, preferably at least 5.0 wt-%, more preferably at least 10.0 wt-%, or at least 30.0 wt-%.

22. The method according to item 20 or 21, wherein the weight ratio of the at least one ketoacid content to the at least one ketoacid dimer content in the feedstock [ketoacid: ketoacid dimer] is in the range of 1:5 to 10:1, preferably 1:3 to 5:1.

23. The method according to any of items 1-22, wherein the feedstock is introduced into the reactor in liquid phase.

24. The method according to any of items 1-23, wherein the second C—C-coupling reaction(s) are conducted at a temperature in the range of 200-400° C., preferably 210-300° C., more preferably 220-280° C., and most preferably 220-260° C.

25. The method according to any of items 1-24, wherein the second C—C-coupling reaction(s) are conducted at a pressure in the range of 0.5-150 bar, preferably 1.0-50 bar, more preferably 1.0-20 bar.

26. The method according to any of items 12-25, wherein the second C—C-coupling reaction(s) are conducted at a weight hourly space velocity (kg feedstock/kg catalyst*h) in the range of 0.05 $h^{-1}$ to 2.0 $h^{-1}$, preferably 0.1 $h^{-1}$ to 1.8 $h^{-1}$, more preferably 0.2 $h^{-1}$ to 1.5 $h^{-1}$, most preferably 0.25 $h^{-1}$ to 1.25 $h^{-1}$.

27. The method according to any of items 1-26, wherein the feedstock comprises at least one of 4-hydroxy-4-methyl-6-oxononanedioic acid, 3-acetyl-4-hydroxy-4methylheptanedioic acid, 5-(2-methyl-5-oxotetrahydrofuran-2-yl)-4-oxopentanoic acid, (E)-4-methyl-6-oxonon-4-enedioic acid, 4-hydroxy-6-methylnonanedioic acid, (E)-6-hydroxy-4-methylnon-4-enedioic acid, (Z)-3-acetyl-4-methylhept-3-enedioic acid, 3-(3-acetyl-2-methyl-5-oxotetrahydrofuran-2-yl)propanoic acid, (Z)-3-1(1-hydroxyethyl)-4-methylhept-3-enedioic acid, and 3-(1-hydroxyethyl)-4-methylheptanedioic acid.

28. A reaction product of the second C—C-coupling reaction(s) obtainable by the method according to any of items 1-27.

29. A method for producing hydrocarbons, the method comprising steps of increasing the molecular weight of a ketoacid using the method according any of items 1-27 to obtain a reaction product and subjecting the reaction product to a hydrodeoxygenation step and optionally to an isomerization step.

30. A hydrocarbon composition obtainable by the method according to item 29.

BRIEF DESCRIPTION OF DRAWINGS

FIG. 2 illustrates possible C—C-coupling reactions of levulinic acid dimers through ketonisation and aldol condensation reaction.

DETAILED DESCRIPTION OF THE INVENTION

One of the challenges in increasing the molecular weight of ketoacids by C—C-coupling reactions is the high reactivity of the product intermediates, which results in too high a degree of oligomerization of the starting components.

The inventors have found that the oligomerization of a ketoacid, specifically of levulinic acid, in the presence of a solid base catalyst such as $K_2O/TiO_2$ results in high formation of coke and tar, which poison the catalyst by blocking the reactive sites on the surface of the catalyst and eventually result in plugging of the reactor. Without being bound to any theory this is suggested to occur due to reactions of levulinic acid to more reactive precursors such as angelica lactones, which are known to have a high tendency to polymerise at temperatures of over 200° C.

The inventors also found that oligomerization of levulinic acid in the presence of an ion exchange resin catalyst such as Amberlyst 70 results in formation of levulinic acid dimers but the yield of higher molecular weight products such as trimers, tetramers and pentamers of levulinic acid remains very small. One of the reasons for the poor performance of the Amberlyst catalyst in formation of higher molecular weight compounds is the requirement of relative low reaction temperatures since the ion exchange catalyst tends to degrade at temperatures of above 200° C.

It was first attempted to reduce the undesired polymerization reactions and to control the oligomerization reactions of levulinic acid by conducting the K2O/TiO2 catalysed reactions in dilute aqueous solutions. The addition of water to suppress coking reactions was, however, found also to decrease the performance of the catalyst system resulting in low yields of the desired oligomerization products.

The invention is based on a surprising finding that the molecular weight of ketoacids can be increased by selective production of ketoacid dimers in the presence of an ion exchange resin catalyst and subsequent oligomerization of the ketoacid dimers to higher molecular weight compounds at a temperature of at least 200° C. Without being bound to any theory, it is suggested that ketoacid dimers are less prone to formation of reactive intermediates at temperatures of above 200° C. and this enables increasing the molecular weight of ketoacid dimers through C—C-coupling reactions while significantly reducing the formation of coke and tar and other undesired polymerization products.

The inventors have also found that the ion exchange resin catalyst is especially suitable for production of certain types of ketoacid dimers, which can be converted to ketoacid trimers, tetramers, hexamers and heptamers at a temperature of at least 200° C.

Accordingly, one aspect the present invention is a method for increasing the molecular weight of a ketoacid as defined in claim 1.

The present invention also relates to a method for increasing the molecular weight of ketoacids.

Ketoacids are organic molecules that have both a keto function (>C=O) as well as a carboxylic acid (COOH) or carboxylate (COO⁻) function. In the present specification special forms of ketoacids include embodiments where the keto function is an aldehyde (—CH=O).

The ketoacid may be an alpha-ketoacid (such as pyruvic acid, oxaloacetic acid and alpha-ketoglutaric acid), beta-ketoacid (such as acetoacetic acid), gamma-ketoacid (such as levulinic acid), or delta-ketoacid. The ketoacid may have more than one keto functionality, and more than one carboxylic acid function. Preferably the ketoacid only has one keto functionality and one carboxylic acid functionality.

Scheme 1

Scheme 1 illustrates exemplary ketoacids according to the present invention, for example where n and m are integers each selected independently of each other from the list consisting of 0, 1, 2, 3, 4, 5, 6, 7, 8, 9, 10 The ketoacid is preferably a gamma ketoacid, more preferably levulinic acid (m=2, n=0).

A ketoacid dimer refers here to a product of a dimerization reaction, in which two ketoacid molecules are coupled together by a C—C-coupling reaction.

Figure 2:
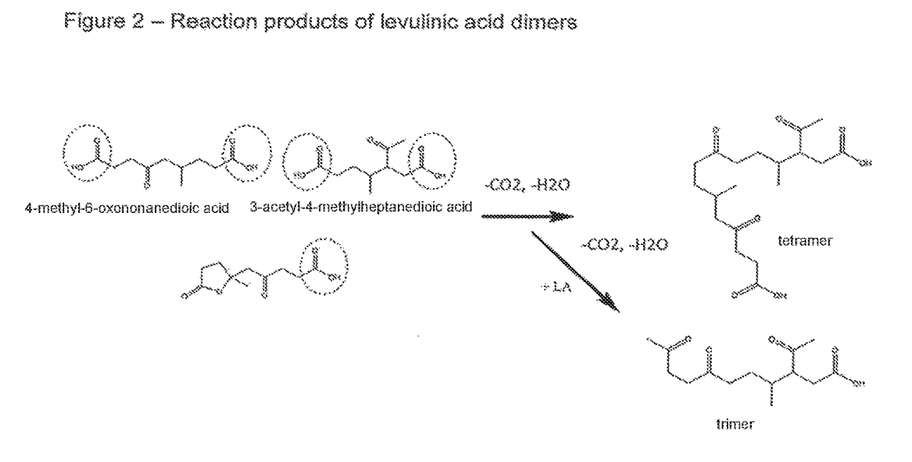
FIG. 2 shows a scheme illustrating some reaction products of some levulinic acid dimers. The figure is not intended to cover all reaction products of levulinic acid dimers, nor is it intended to show all types of levulinic acid dimers.

Preferably more than 15 wt % of the reaction product may be determined to belong to the group containing trimerisation, tetramerisation, pentamerisation, and hexamerisation products of ketoacid. By trimerisation, tetramerisation, pentamerisation and hexamerisation products is meant reaction products relating to three, four, five and six molecules of one or more of ketoacid units being coupled together, respectively. The reactions may occur between ketoacid dimers or between ketoacids and ketoacid dimers as shown in FIG. 2. Usually the majority of the remainder of the reaction product (i.e. excluding the trimerisation, tetramerisation, pentamerisation, and hexamerisation products of ketoacid) corresponds to non-reacted material.

In the case of a feedstock comprising ketoacid derivatives in addition to ketoacid dimers and ketoacids, the trimerisation, tetramerisation, pentamerisation, and hexamerisation products may additionally contain mixed C—C-coupling products comprising one or more ketoacids units and/or derivatives thereof.

In the present invention the molecular weight of the keto acids and ketoacid dimers are increased through one or more types of C—C-coupling reaction(s). Many types of C—C-coupling reactions are known in the art, and the skilled person would be able to identify such C—C-coupling reactions based on the reaction conditions provided. In particular the C—C-coupling reactions may be ketonisation reactions or reactions proceeding through an enol or enolate intermediate. Preferably, the C—C-coupling reactions are selected from the list comprising: aldol-type reactions and condensations, ketonisations, reactions where the C—C-coupling involves an alkene, as well as other oligomerization reactions. The C—C-coupling reactions may proceed with two identical molecules or may be a crossed reaction between two different molecules.

The at least one ketoacid dimer preferably contains a γ-ketoacid dimer, most preferably levulinic acid dimer. In addition, one or more further ketoacid dimers may be employed.

Preferably, the first and second C—C-coupling reaction(s) are conducted in a first and in a second reactor, respectively.

Preferably the feedstock comprises as the major component one or more ketoacid dimers, for example in some embodiments the content of the at least one ketoacid dimer in the feedstock is at least 30 wt-% such as at least 40 wt-%, at least 50 wt-%, at least 55 wt-%, or at least 60 wt-%.

Preferably the content of water in the feedstock is less than 5.0 wt-%, preferably less than 2.0 wt-%, more preferably less than 1.0 wt-%. In some embodiments no water is present in the feedstock, but internal water may be produced in some condensation reactions.

The conversion of ketoacid dimers to desired C—C-coupling reaction products was found to increase as the content of ketoacid dimer in the feedstock increased. Presence of water was found to decrease the reactions of ketocids to coke precursors but addition of water also decreased catalyst activity and the yield of desired C—C-coupling reaction products was lowered. The yield of C—C-coupling products has to be high enough to enable an economically feasible process for production of fuel components and chemicals from ketoacids.

In addition to ketoacid dimers, the feedstock may also contain aldehydes, such as furfural or hydroxymethylfurfural.

In the step of subjecting the raw material to first C—C-coupling reaction(s), the at least one ketoacid undergoes at least one C—C-coupling reaction with another ketoacid or ketoacid derivative present in the raw material so as to produce a ketoacid dimer.

The ion exchange catalyst has been found particularly suitable for obtaining high degree of ketoacid dimers, which can be upgraded to higher molecular weight components in the presence of a solid base catalyst system.

Preferably the at least one ketoacid in the raw material is a γ-ketoacid, preferably levulinic acid.

The reactivity of an IER catalyst with a particular reactant is determined by the average pore diameter of the catalyst. Preferably the average pore diameter of the ion exchange resin catalyst is in the range of 150-300 Å, preferably 200-250 Å.

Preferably the raw material is subjected to the first C—C-coupling reaction(s) at a temperature of 100-190° C., preferably 120-160° C., more preferably 120-140° C. This temperature range was found to be particularly suitable for obtaining a high yield of ketoacid dimers suitable to be used as the at least one ketoacid dimer in the second C—C-coupling reactions.

It has also been found that the stability of the ion exchange catalyst and the yield of dimers can be improved if the raw material is subjected to C—C-coupling reactions in the presence of hydrogen and if the ion exchange resin catalyst comprises a hydrogenating metal. Preferably the ion exchange resin catalyst comprises a hydrogenating metal selected from a group of Ni, Mo, Co, Ru, Rh, Pd, Pt, or a combination of these.

A solid metal oxide catalyst system comprising a first and a second metal oxide has been found to catalyze multiple types of C—C-coupling reactions between ketoacid dimers and monomers of ketoacids and to simultaneously to suppress the coking tendency of the reaction intermediates.

The reactivity of a catalyst depends on the number the active sites on the surface of the catalyst and on the specific surface are of the catalyst. According to one embodiment, the solid base catalyst has a specific surface area of from 10 to 500 $m^2$/g. The catalyst system having a specific surface area in these ranges have shown to provide enough reactivity with ketoacid dimers to obtain high yield of desired C—C-coupling reaction products such as trimers, tetramers, pentamers, hexamers and heptamers of a ketoacid but at the same time to minimize the reactions of ketoacids to coke precursors.

Preferably the first metal oxide comprises an oxide of one of K, Li, Be B, Na, Mg, Al, Si, Ca, Sc, Ti, V, Cr, Mn, Fe, Co, Ni, Cu, Zn, Br, Sr, Y, Zr, Nb, Mo, Ba, W, Pb, Bi, La, Ce, Th, and the second metal oxide comprises an oxide of one of K, Li, Be B, Na, Mg, Al, Si, Ca, Sc, Ti, V, Cr, Mn, Fe, Co, Ni, Cu, Zn, Br, Sr, Y, Zr, Nb, Mo, Ba, W, Pb, Bi, La, Ce, Th or a combination of these, the first metal oxide not being same as second metal oxide. Combinations of metal oxides include mixtures of individual metal oxides (solid solutions), mixed metal oxides and supported metal oxides.

Preferably the first metal oxide comprises an oxide of one of K, W, Li, Be B, Na, Mg, Al, Si, Ca, Sr, and Ba and the second metal oxide comprises an oxide of one of Ti, Sc, V, Cr, Mn, Fe, Co, Ni, Cu, Zn, Br, Sr, Y, Zr, Nb, Mo, Ba, W, Pb, Bi, La, Ce, Th, or a combination of these.

These oxides have shown to provide good reaction properties in catalysing the second C—C-coupling reactions.

Furthermore, the carriers mentioned above have shown to provide good carrier properties without affecting the function of the more active part, including a synergistic interaction. Moreover, the combinations mentioned above allow using the catalyst for a long period of time without deterioration and/or dissolution in the acidic reaction medium and thus allow for reduced overall catalyst consumption.

Preferably, the first metal oxide comprises potassium oxide and the second metal oxide comprises titanium oxide, preferably the potassium oxide being supported on a titanium oxide carrier.

Preferably, the catalyst system comprises tungsten oxide or ceria supported on a metal oxide carrier, wherein the carrier is preferably selected from the group consisting of zirconia, titania, silica, vanadium oxide, chromium oxide, preferably zirconia or titania.

The second C—C-coupling reactions in the presence of $K_2O/TiO_2$ catalyst are suggested to proceed by ketonization reactions, in which reactions the molecular weight of ketoacid dimer is increased and simultaneously a significant amount of oxygen is removed. The loss of oxygen in the second C—C-coupling reactions is favourable in the production of hydrocarbons from ketoacids since removal of oxygen in a hydrodeoxygenation step consumes a lot of hydrogen, which increases the process costs and also decreases the $CO_2$ emission reductions in case hydrogen produced from fossil raw material is used in the hydrodeoxygenation step. In addition, the keto groups formed in the second C—C-coupling reactions have been found to be easily hydrotreated, which enables use of lower reaction temperatures in the hydrodeoxygenation step. Use of lower hydrodeoxygenation temperatures also decreases the cyclisation tendency of the C—C-coupling products.

Preferably the content of the first metal oxide in the catalyst system is 1.0 to 40.0 wt-%, preferably 2.0 to 30.0 wt-%, further preferably 13.0 to 30.0 wt-%, calculated by weight of the metal oxide in relation to the total mass of the catalyst.

Preferably the feedstock further comprises at least one ketoacid, preferably a γ-ketoacid, more preferably levulinic acid.

Preferably the content of the at least one ketoacid in the feedstock is at least 1.0 wt-%, preferably at least 5.0 wt-%, more preferably at least 10.0 wt-%, or at least 30.0 wt-%.

Preferably the weight ratio of the content of the at least one ketoacid to the content of the at least one ketoacid dimer in the feedstock is in the range of 1:5 to 10:1, preferably 1:3 to 5:1.

Preferably the feedstock comprises a mixture of a ketoacid dimer in combination with ketoacid dimer derivatives, such as at least 30 wt-% of ketoacid dimer and at least 10 wt-% of ketoacid dimer derivative(s) based on the total mass of feedstock.

Preferably the feedstock is fed into in a single reactor, or into single reactor bed. The reactor should be able to be pressurised, and to accommodate the feedstock and the catalyst system, if present. The reactor should have means, such as one or more inlets and/or outlets, for supplying gases and adding/withdrawing feedstock. In addition, means for controlling the temperature or the pressure and the temperature are preferably present.

The reaction temperature has been found to have a significant effect on the product distribution. At temperatures below 200° C. the yield of C—C-coupling products of ketoacid dimers in the second C—C-coupling reaction(s) is too low and at temperatures above 400° C. the yield may be decreased due to formation coke in other non-desired polymerization products. The second C—C-coupling reaction(s) are preferably conducted at a temperature in the range of 200-400° C., more preferably 210-300° C., even more preferably 220-280° C. and still more preferably 220-260° C. The above cited temperature ranges were found to be particularly suitable for obtaining a high degree of reaction products comprising more than two ketoacid units (C13-C30) while avoiding excessive polymerization and coking of the catalyst.

Since most of the second C—C-coupling reactions take place in liquid phase the pressure and temperature are suitably selected to keep the reactants in liquid phase. According to one embodiment the C—C-coupling reaction(s) are conducted at a pressure of 0.5-100.0 bar, preferably 1.0-50 bar, more preferably 1.0-20 bar.

Preferably the second C—C-coupling reactions are conducted at a weight hourly space velocity (kg feedstock/kg catalyst*hour) of 0.05 $h^{-1}$ to 2.0 $h^{-1}$, preferably 0.1 $l^{-1}$ to 1.8 $h^{-1}$, more preferably 0.2 $h^{-1}$ to 1.5 $h^{-1}$, most preferably 0.25 $h^{-1}$ to 1.25 $h^{-1}$. The WHSV has an influence on the composition of the resulting material, since it determines the effective contact time of reagent and catalyst. The abovementioned ranges have shown to provide a high degree of favourable products.

The second C—C coupling reaction(s) may proceed in the presence of hydrogen. The hydrogen may be mixed with one or more other gases, preferably an inert gas such as nitrogen, argon, helium or another of the noble gases, or gas behaving inertly to the reaction conditions of the present invention. By behaving inertly it is considered that the gas should not to a major extent participate as a reaction member, and preferably the inert gas should participate as little as possible, such as not participate at all. The hydrogen addition will usually not introduce hydrogenation activity unless the solid metal oxide catalyst system comprises a hydrogenation metal but it is proposed to modify the surface properties of the reducible metal oxide which is part of the catalyst system.

Preferably, the second C—C-coupling reactions are conducted at a flow ratio (H2/feedstock) of 100-3000 Nl/l, preferably 200-2000 Nl/l, more preferably 500-1800 Nl/l and most preferably 500-1500 Nl/l.

Preferably, the feed ratio of nitrogen (N2/liquid feedstock) is 100-3000 Nl/l, preferably 200-2000 Nl/l, more preferably 500-1800 Nl/l and most preferably 500-1500 Nl/l. The combined use of hydrogen and nitrogen showed particularly favourable results.

Preferably, the solid metal oxide catalyst system comprises a hydrogenation metal in addition to the first and second metal oxides. The hydrogenation metal is preferably selected from Ru, Rh, Pd, and Pt or a combination of these. A catalyst system comprising a hydrogenation metal was found to further increase the stability of the catalyst and to suppress the oligomerization reactions of ketoacid dimers to components not suitable for use as fuel components or chemicals.)

Preferably the at least one ketoacid dimer is selected from a group of 4-hydroxy-4-methyl-6-oxononanedioic acid, 3-acetyl-4-hydroxy-4-methylheptanedioic acid, 5-(2-methyl-5-oxotetrahydrofuran-2-yl)-4-oxopentanoic acid, (E)-4-methyl-6-oxonon-4-enedioic acid, 4-hydroxy-6-methylnonanedioic acid, (E)-6-hydroxy-4-methylnon-4-enedioic acid, (Z)-3-acetyl-4-methylhept-3-enedioic acid, 3-(3-acetyl-2-methyl-5-oxotetrahydrofuran-2-yl)propanoic acid, (Z)-3-1(1-hydroxyethyl)-4-methylhept-3-enedioic acid, 3-(1-hydroxyethyl)-4-methylheptanedioic acid, or a combination thereof.

The raw material may be obtained from processing of lignocellulosic material, and such processed material may be used directly, or purified to varying degrees before being used as a raw material in the method of the present invention. The levulinic acid may be produced e.g. with the Biofine method disclosed in U.S. Pat. No. 5,608,105.

In another aspect of the present invention, reaction product obtainable by the method according to the present invention is provided. This product may be directly used as fuel or base oil components or chemicals or as intermediate components in production of fuel or base oil components or chemicals.

The reaction product obtainable by the method of the present invention may—if desired—be further subjected to a hydrodeoxygenation (HDO) step to remove oxygen, which in some embodiments produces completely deoxygenated material (i.e. hydrocarbon compounds having no oxygen atoms). The produced hydrocarbons may be used as fuel or base oil components or chemicals or as starting components in the production of fuel or base oil components or chemicals. The hydrodeoxygenated products may also be further isomerized to e.g. isoparaffins.

One of the advantages of the present invention is that ketoacids produced from renewable materials can be upgraded to higher molecular weight hydrocarbons and/or hydrocarbon derivatives, which may be used as fuel or base oil components or chemicals or as starting components in the production of fuel or base oil components or chemicals.

Figure 3:
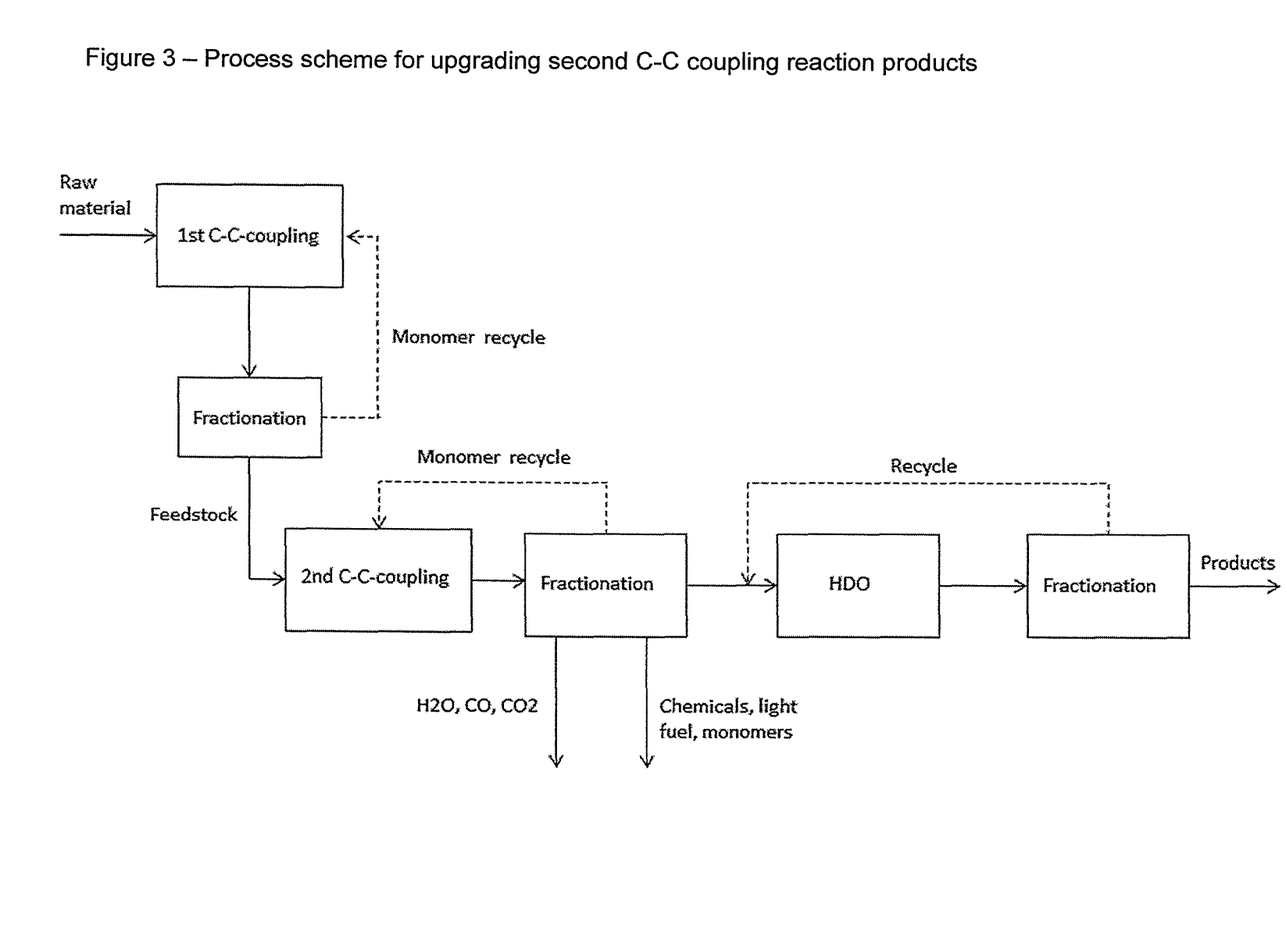
FIG. 3 shows an overview of a possible process scheme for further upgrading the products from the C—C-coupling reactions.
Figure 4:
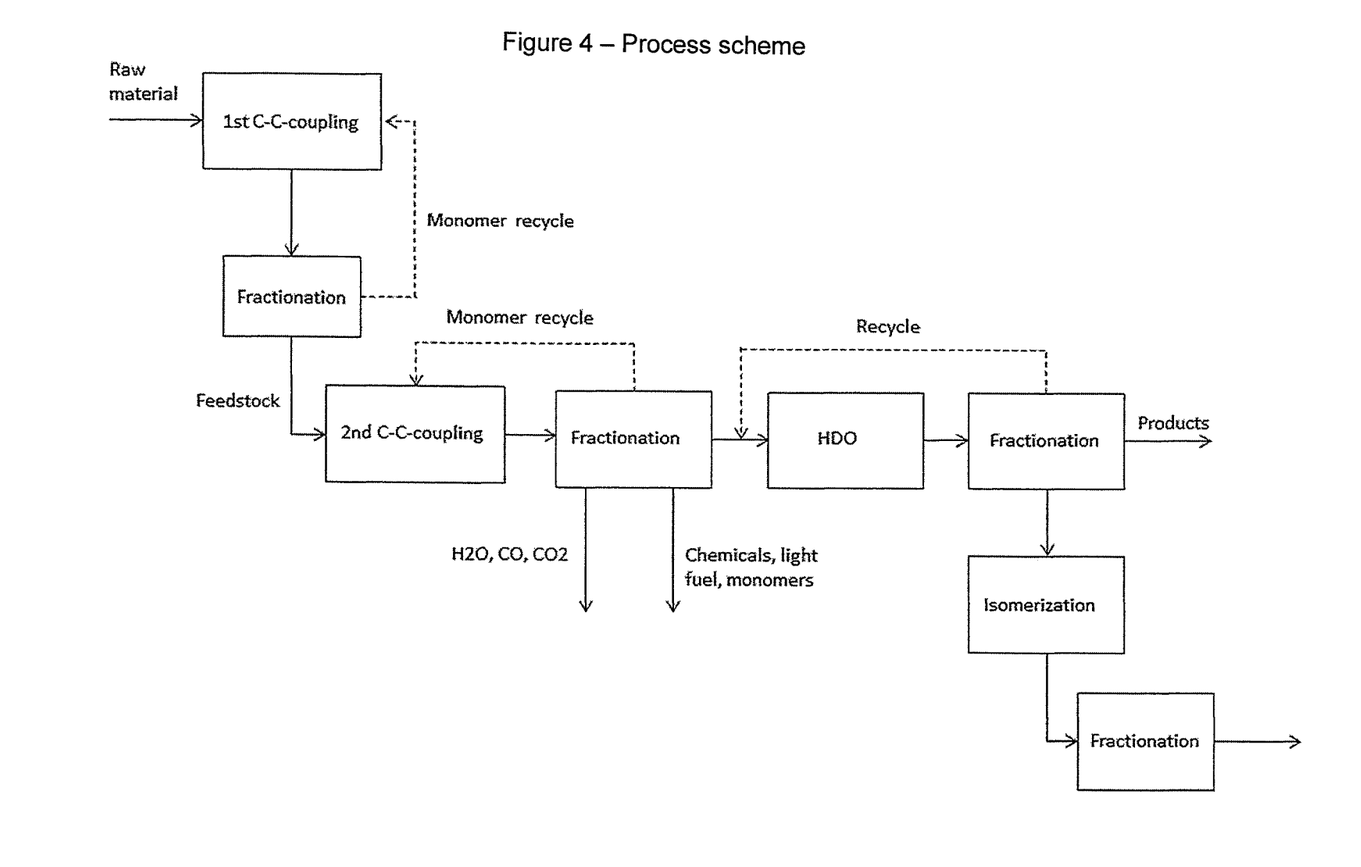
FIG. 4 shows an overview of a possible process scheme for preparing and upgrading the products from the C—C-coupling reactions.

The reaction products from the first and/or second C—C-coupling reactions may be fractionated to remove potential unreacted ketoacid monomers and other light components such as water and $CO_2$ formed in the first and second C—C-coupling reactions from the reaction products as illustrated in FIG. 3. The fractionation can be conducted by any conventional means such as distillation. The unreacted ketoacid monomer may optionally be recycled and combined with the feed of the first reactor.

Another aspect of the present invention involves a method for production of hydrocarbons, the method comprising steps of increasing the molecular weight of a ketoacid using the method of the present invention to obtain reaction product and subjecting the reaction product to a hydrodeoxygenation step and optionally to an isomerization step.

Preferably, the HDO catalyst employed in the hydrodeoxygenation step comprises a hydrogenation metal on a support, such as for example a HDO catalyst selected from a group consisting of Pd, Pt, Ni, Co, Mo, Ru, Rh, W or any combination of these. The hydrodeoxygenation step may for example be conducted at a temperature of 100-500° C. and at a pressure of 10-150 bar.

Water and light gases may be separated from the HDO product with any conventional means such as distillation. After the removal of water and light gases the HDO product may be fractionated to one or more fractions suitable for use as gasoline, aviation fuel, diesel or base oil components. The fractionation may be conducted by any conventional means, such as distillation. Optionally part of the product of the HDO step may be recycled and combined to the feed of the HDO reactor.

Another aspect of the present invention involves a hydrocarbon composition obtainable by the method according to the present invention. This product may be used as fuel or base oil components or chemicals or as intermediate components in production of fuel or base oil components or chemicals.

The product of the hydrodeoxygenation step may also be subjected to an isomerization step in the presence of hydrogen and an isomerization catalyst. Both the hydrodeoxygenation step and isomerisation step may be conducted in the same reactor. In some embodiments the isomerisation catalyst is a noble metal bifunctional catalyst, for example Pt-SAPO or Pt-ZSM-catalyst. The isomerization step may for example be conducted at a temperature of 200-400° C. and at a pressure of 20-150 bar.

It is preferred that only a part of the HDO product is subjected to an isomerization step, in particular the part of HDO product which is subjected to isomerization may be the heavy fraction boiling at or above a temperature of 300° C.

The hydrocarbon product obtainable from the hydrodeoxygenation and/or the isomerisation step may be used as fuel or base oil components or chemicals or as intermediate components in production of fuel or base oil components or chemicals.

Generally the choice of subjecting HDO product to isomeration is highly dependable of the desired properties of the end products. In case the HDO product contains a high amount of n-paraffins, the HDO product may be subjected to isomerization step to convert at least part of the n-paraffins to isoparaffins to improve the cold properties of the end product.

EXAMPLES

Materials

As example catalysts, Amberlyst CH 28-catalyst, $K_2O$/$TiO_2$-catalyst and $WO_3$/$ZrO_2$-catalyst were used in first and second C—C-coupling reactions of levulinic acid and levulinic acid dimers, respectively. The $K_2O$/$TiO_2$-catalyst is available from BASF and the $WO_3$/$ZrO_2$-catalyst is available from Saint-Gobain NORPRO. The composition of the $K_2O$/$TiO_2$-catalyst is shown in Table 1.

TABLE 1

| Composition of the $K_2O$/$TiO_2$-catalyst $K_2O$/$TiO_2$ | |
|---|---|
| Type | KEC25 |
| $TiO_2$, wt-% | 96.7 |
| $K_2O$, wt-% | 2.4 |
| $Nb_2O$, wt-% | 0.1 |
| $Ce_2O_3$, wt-% | 0.3 |
| Others, wt-% | 0.5 |

The $WO_3$/$ZrO_2$-catalyst (type SZ 6*143) had a surface area of 130 $m^2$/g and a $WO_3$ content of 18 wt-% calculated by total mass of the catalyst. The Amberlyst CH 28-catalyst was a Pd-doped ion exchange resin catalyst with an average pore diameter of 260 Å and Pd content of 0.7 wt-%.

The specific surface area and tungsten oxide content of the WO3/$ZrO_2$-catalyst and the average pore diameter of the Amberlyst CH 28 IER-catalyst have been provided by the catalyst manufacturers.

Example 1

Increasing the Molecular Weight of Levulinic Acid Dimers by Second C—C Coupling Reactions with $K_2O$/$TiO_2$-Catalyst System The performance of $K_2O$/$TiO_2$-catalyst was evaluated in a reactor test run with a feedstock comprising 43 wt-parts of levulinic acid, and 55 wt-parts of levulinic acid dimers and 2 wt-parts of levulinic acid oligomers.

The feedstock was obtained by reacting commercial grade levulinic acid (97 wt-%) in the presence of Amberlyst CH 28 catalyst (trade name; Pd doped ion exchange resin) at a temperature of 130° C., pressure of 20 bar, WHSV of 0.2 $h^{-1}$ and hydrogen to liquid raw material ratio of 1350 Nl/l. The feedstock was prepared in a tubular reactor. Also 2 wt-% of $H_2O$ was continuously added to stabilize catalyst activity. WHSV and hydrogen to organic material ratio is calculated from the amount of liquid raw material fed into the reactor.

The second C—C coupling reactions for the feedstock were conducted in a continuous tubular fixed bed type reactor at temperatures ranging from about 220° C. to about 250° C. and under a pressure of about 1 bar, using a weight hourly space velocity (WHSV) of 0.7 $h^{-1}$. The reactions were conducted in nitrogen flow (10 l/h) to study the effect of hydrogen added to the feedstock. WHSV was calculated from the amount of monomers, dimers and oligomers (=liquid feedstock) fed into the reaction vessel.

For reactions at various conditions the amount of gas formed was determined from the liquid yield (gas=100−liquid product). The liquid product consists of the organic phase including water formed in the reaction.

The quantitative amount of LA in liquid product was determined by HPLC analysis. The relative amount of dimers and oligomers in the organic phase was obtained from GPC chromatograms. The composition of the organic phase, —including unreacted LA, was calculated relative to the liquid product.

The product yields and compositions of the liquid phase for conversion of levulinic acid on $K_2O$/$TiO_2$ catalyst system in nitrogen flow are presented in Tables 2 and 3.

TABLE 2

Process conditions and product yields with $K_2O$/$TiO_2$-catalyst.

| Process conditions | | | | Product yield | | |
|---|---|---|---|---|---|---|
| Temperature ° C. | Pressure range bar | Gas flow l/h | WHSV h-1 | Gas wt-% | Liquid yield wt-% | Experiment |
| 220 | 1-3 | 10 | 0.7 | 3 | 97 | EX 1 |
| 240 | 1-3 | 10 | 0.7 | 6 | 94 | EX 2 |
| 250 | 1-3 | 10 | 0.7 | 9 | 91 | EX 3 |

TABLE 3

Product distribution in the organic phase with $K_2O$/$TiO_2$-catalyst determined by GPC peak areas.

| Composition of organic phase | | | | |
|---|---|---|---|---|
| LA area-% | Lactone dimers area-% | Diacid dimers area-% | Oligomers area-% | Experiment |
| 28 | 17 | 52 | 3 | FEED |
| 27 | 32 | 26 | 15 | EX 1 |
| 28 | 29 | 17 | 26 | EX 2 |
| 26 | 27 | 13 | 35 | EX 3 |

Example 2

Increasing the Molecular Weight of Levulinic Acid Dimers by Second C—C Coupling Reactions with WO$_3$/ZrO$_2$ Metal Oxide Catalyst The performance of WO$_3$/ZrO$_2$ catalyst was evaluated in a reactor test run with a feedstock comprising 43 wt-parts of levulinic acid, and 53 wt-parts of levulinic acid dimers and 2 wt-parts of levulinic acid oligomers.

The feedstock was obtained in the same manner as in Example 1.

The second C—C coupling reactions for the feedstock were conducted in a continuous tubular fixed bed type micro reactor at temperatures ranging from about 200° C. to about 270° C. and under a pressure of about 20 bar, using a weight hourly space velocity (WHSV) of 0.5 h$^{-1}$. The reactions were conducted in nitrogen flow (3 l/h) at temperatures of 240° C. and below and in hydrogen flow (3 l/h) at temperatures of above 240° C. WHSV was calculated from the amount of monomers, dimers and oligomers (=liquid feedstock) fed into the reaction vessel.

For reactions at various conditions the amount of gas formed was determined from the liquid yield (gas=100−liquid product). The liquid product consists of the organic phase including water formed in the reaction.

The quantitative amount of LA (levulinic acid) in liquid product was determined by HPLC analysis. The relative amount of dimers and oligomers in the organic phase was obtained from GPC chromatograms. The composition of the organic phase, —including unreacted LA, was calculated relative to the liquid product.

The composition of the organic phase was determined by GPC (area-%).

The product yields and compositions of the liquid phase for conversion of levulinic acid dimers on WO$_3$/ZrO$_2$ catalyst system in nitrogen and hydrogen flow are presented in Tables 4 and 5.

TABLE 4

Process conditions and product yields with WO$_3$/ZrO$_2$-catalyst.

| Process conditions | | | | Gas and liquid Yields | | |
|---|---|---|---|---|---|---|
| Temperature ° C. | Pressure bar | Gas flow | WHSV h$^{-1}$ | Gas phase wt-% | Liquid phase wt-% | Experiment |
| 200 | 20 | N$_2$ | 0.5 | — | 100 | EX 4 |
| 220 | 20 | N$_2$ | 0.5 | — | 100 | EX 5 |
| 240 | 20 | N$_2$ | 0.5 | 5 | 95 | EX 6 |
| 250 | 20 | H$_2$ | 0.5 | 5 | 95 | EX 7 |
| 260 | 20 | H$_2$ | 0.5 | 10 | 90 | EX 8 |
| 270 | 20 | H$_2$ | 0.5 | 10 | 90 | EX 9 |

The liquid phase contains organic oxygenates (=organic phase) and water. The amount of water in liquid phase was not determined.

TABLE 5

Product distribution in the liquid phase with WO$_3$/ZrO$_2$-catalyst determined by GPC peak areas.

| Composition of organic phase | | | | |
|---|---|---|---|---|
| LA area-% | Lactone dimers area-% | Diacid dimers area-% | Oligomers area-% | Experiment |
| 28 | 17 | 52 | 3 | FEED |
| 26 | 30 | 38 | 6 | EX 4 |
| 24 | 33 | 33 | 10 | EX 5 |
| 22 | 33 | 21 | 24 | EX 6 |
| 26 | 35 | 20 | 19 | EX 7 |
| 24 | 33 | 16 | 27 | EX 8 |
| 23 | 29 | 15 | 34 | EX 9 |

Example 3

Increasing the Molecular Weight of Levulinic Acid Dimers by Thermal C—C Coupling Reactions Oligomers of levulinic acid were produced by subjecting the same feedstock as used in Examples 1 and 2 to thermal C—C-coupling reactions at temperatures of above 200° C. and in the absence of catalyst.

The thermal C—C coupling reactions for the feedstock were conducted in a continuous tubular reactor at temperatures ranging from about 220° C. to about 250° C. and under a pressure of about 2 bar. The reactions were conducted in 10 l/h of helium, nitrogen or hydrogen flow and also without any gas flow.

For reactions at various conditions the amount of gas formed was determined from the liquid yield (gas=100−liquid product). The liquid product consists of the organic phase including water formed in the reaction.

The quantitative amount of LA (levulinic acid) in liquid product was determined by HPLC analysis. The relative amount of dimers and oligomers in the organic phase was obtained from GPC chromatograms. The composition of the organic phase, including unreacted LA, was calculated relative to the liquid product.

The product yields and compositions of the liquid phase for conversion of levulinic acid dimers with thermal C—C-coupling reactions are presented in Tables 6 and 7.

TABLE 6

Process conditions and product yields with thermal C-C-coupling reactions.

| Process conditions | | | Product yield | | |
|---|---|---|---|---|---|
| Temperature ° C | Pressure bar | Gas flow | Gas wt-% | Liquid yield wt-% | Experiment |
| 220 | 2 | He | 6.4 | 93.6 | EX 10 |
| 240 | 2 | He | 7.8 | 92.2 | EX 11 |
| 250 | 2 | He | 9.1 | 90.9 | EX 12 |
| 220 | 2 | N$_2$ | 2.5 | 97.5 | EX 13 |
| 240 | 2 | N$_2$ | 6.1 | 93.9 | EX 14 |
| 250 | 2 | N$_2$ | 4.8 | 95.2 | EX 15 |
| 220 | 2 | H$_2$ | 2.5 | 97.5 | EX 16 |
| 240 | 2 | H$_2$ | 2.7 | 97.3 | EX 17 |
| 250 | 2 | H$_2$ | 9.6 | 90.4 | EX 18 |
| 220 | 2 | None | 0.0 | 100.0 | EX 19 |
| 240 | 2 | None | 1.4 | 98.6 | EX 20 |
| 250 | 2 | None | 5.0 | 95.0 | EX 21 |

TABLE 7

Product distribution in the liquid phase with thermal C-C-coupling reactions determined by GPC peak areas.

Composition of organic phase

| LA area-% | Lactone dimers area-% | Diacid dimers area-% | Oligomers area-% | Experiment |
|---|---|---|---|---|
| 28 | 17 | 52 | 3 | FEED |
| 25 | 33 | 26 | 16 | EX 10 |
| 22 | 26 | 13 | 39 | EX 11 |
| 19 | 19 | 10 | 52 | EX 12 |
| 31 | 31 | 28 | 16 | EX 13 |
| 27 | 27 | 14 | 34 | EX 14 |
| 22 | 22 | 11 | 45 | EX 15 |
| 28 | 32 | 33 | 8 | EX 16 |
| 29 | 33 | 23 | 15 | EX 17 |
| 29 | 30 | 18 | 24 | EX 18 |
| 27 | 28 | 41 | 5 | EX 19 |
| 27 | 33 | 34 | 7 | EX 20 |
| 29 | 34 | 29 | 8 | EX 21 |

In none of the Experiments of Examples 1 to 3, a significant degree of coke or tar formation was recognized after 40 days of continuous reaction. Furthermore, it can be confirmed from the above results, that oligomerization of ketoacid dimers produced at low temperature from ketoacid monomers proceeds at temperatures at and above 200° C. The resulting products had a molecular weight distribution suitable for further conversion to fuel or baseoil components and/or chemicals.

The invention claimed is:

1. A method for increasing the molecular weight of a ketoacid, the method comprising:
   providing in a reactor a raw material having at least one ketoacid, wherein the ketoacid is an organic molecule that has a keto or aldehyde function and a carboxylic acid or carboxylate function;
   subjecting the raw material to first C—C-coupling reaction(s) in a presence of an ion exchange resin catalyst so as to produce at least one ketoacid dimer;
   providing in a reactor a feedstock having the at least one ketoacid dimer; and
   subjecting the feedstock to second C—C-coupling reaction(s) at a temperature of at least 200° C.

2. The method according to claim 1, wherein the at least one ketoacid dimer is a dimer of a γ-ketoacid; and/or
   wherein the content of the at least one ketoacid dimer in the feedstock is at least 30 wt-%.

3. The method according to claim 1, wherein the first and second C—C-coupling reaction(s) are conducted in first and second reactors, respectively.

4. The method according to claim 1, wherein the content of water in the feedstock is less than 15.0 wt-%.

5. The method according to claim 1, wherein the at least one ketoacid in the raw material is γ-ketoacid; and/or
   wherein an average pore diameter of the ion exchange resin catalyst is in the range of 150-300 Å; and/or
   wherein the first C—C-coupling reaction(s) are conducted at a temperature in the range of 100-190° C.

6. The method according to claim 1, wherein the raw material is subjected to the first C—C-coupling reaction(s) in the presence of hydrogen, wherein the ion exchange resin catalyst includes at least one hydrogenating metal selected from Group VIII of the Periodic Table of Elements.

7. The method according to claim 1, wherein the feedstock is subjected to the second C—C-coupling reactions in the absence of a catalyst.

8. The method according to claim 1, wherein the feedstock is subjected to the second C—C-coupling reaction(s) in the presence of a solid metal oxide catalyst system having a first metal oxide and a second metal oxide.

9. The method according to claim 8, wherein the catalyst system has a specific surface area of from 10 to 500 $m^2/g$; and/or
   wherein the solid catalyst system includes a mixture in which the first metal oxide is supported on the second metal oxide; and/or
   wherein the surface density of metal atoms of the first metal oxide supported on the second metal oxide is from 0.5 to 20 metal atoms/$nm^2$; and/or
   wherein the first metal oxide includes an oxide of one of K, Li, Be, B, Na, Mg, Al, Si, Ca, Sc, Ti, V, Cr, Mn, Fe, Co, Ni, Cu, Zn, Br, Sr, Y, Zr, Nb, Mo, Ba, W, Pb, Bi, La, Ce, Th and the second metal oxide includes one of K, Li, Be B, Na, Mg, Al, Si, Ca, Sc, Ti, V, Cr, Mn, Fe, Co, Ni, Cu, Zn, Br, Sr, Y, Zr, Nb, Mo, Ba, W, Pb, Bi, La, Ce, Th, or a combination of these, the first metal oxide not being same as second metal oxide; and/or
   wherein the first metal oxide includes an oxide of potassium and the second metal oxide includes an oxide of titanium, or the first metal oxide includes an oxide of tungsten or cerium and the second metal oxide includes an oxide of zirconium, titanium, silicon, vanadium, or chromium, or includes an oxide of zirconium or titanium; and/or
   wherein the content of the first metal oxide in the catalyst system is 1.0 to 40.0 wt %, calculated by weight of metal oxide relative to the total mass of the catalyst.

10. The method according to claim 1, wherein the feedstock comprises:
    at least one ketoacid.

11. The method according to claim 10, wherein the content of the at least one ketoacid in the feedstock is at least 1.0 wt-%; and/or
    wherein the weight ratio of the at least one ketoacid content to the at least one ketoacid dimer content in the feedstock [ketoacid:ketoacid dimer] is in the range of 1:5 to 10:1.

12. The method according to claim 1, wherein the feedstock is introduced into the reactor in liquid phase; and/or
    wherein the second C—C-coupling reaction(s) are conducted at a temperature in the range of 200-400° C.; and/or
    wherein the second C—C-coupling reaction(s) are conducted at a pressure in the range of 0.5-150 bar; and/or
    wherein the second C—C-coupling reaction(s) are conducted at a weight hourly space velocity (kg feedstock/kg catalyst*h) in the range of 0.05 $h^{-1}$ to 2.0 $h^{-1}$; and/or
    wherein the feedstock includes at least one of 4-hydroxy-4-methyl-6-oxononanedioic acid, 3-acetyl-4-hydroxy-4-methylheptanedioic acid, 5-(2-methyl-5-oxotetrahydrofuran-2-yl)-4-oxopentanoic acid, (E)-4-methyl-6-oxonon-4-enedioic acid, 4-hydroxy-6-methylnonanedioic acid, (E)-6-hydroxy-4-methylnon-4-enedioic acid, (Z)-3-acetyl-4-methylhept-3-enedioic acid, 3-(3-acetyl-2-methyl-5-oxotetrahydrofuran-2-yl) propanoic acid, (Z)-3-1(1-hydroxyethyl)-4-methyl-hept-3-enedioic acid, and 3-(1-hydroxyethyl)-4-methylheptanedioic acid.

13. A reaction product of the second C—C-coupling reaction(s) obtained by the method according to claim 1.

14. A method for producing hydrocarbons, the method comprising:

increasing the molecular weight of a ketoacid using the method according to claim 1 to obtain a reaction product, and subjecting the reaction product to a hydrodeoxygenation step and optionally to an isomerization step.

15. A hydrocarbon composition obtained by the method according to claim 14, wherein the reaction product comprises a compound selected from the group consisting of a trimer of the ketoacid, a tetramer of the ketoacid, a pentamer of the ketoacid, a hexamer of the ketoacid, and a heptamer of the ketoacid.

16. The method according to claim 1, wherein the at least one ketoacid dimer is a dimer of levulinic acid; and/or
  wherein the content of the at least one ketoacid dimer in the feedstock is at least 60 wt-%.

17. The method according to claim 2, wherein the first and second C—C-coupling reaction(s) are conducted in first and second reactors, respectively.

18. The method according to claim 1, wherein the content of water in the feedstock is less than 5.0 wt-%.

19. The method according to claim 17, wherein the at least one ketoacid in the raw material is levulinic acid; and/or
  wherein the average pore diameter of the ion exchange resin catalyst in the range of 200-250 Å; and/or
  wherein the first C—C-coupling reaction(s) are conducted at a temperature in the range of 120-140° C.

20. The method according to claim 18, wherein the raw material is subjected to the first C—C-coupling reaction(s) in the presence of hydrogen, wherein the ion exchange resin catalyst includes at least one hydrogenating metal selected from Group VIII of the Periodic Table of Elements:
  Co, Ni, Ru, Rh, Pd, and Pt.

21. The method according to claim 8, wherein the catalyst system has a specific surface area of from 10 to 500 $m^2/g$; and/or
  wherein the solid catalyst system includes a mixture in which the first metal oxide is supported on the second metal oxide; and/or
  wherein the surface density of metal atoms of the first metal oxide supported on the second metal oxide is from 0.5 to 20 metal atoms/$nm^2$; and/or
  wherein the first metal oxide includes an oxide of one of K, Li, Be, B, Na, Mg, Al, Si, Ca, Sc, Ti, V, Cr, Mn, Fe, Co, Ni, Cu, Zn, Br, Sr, Y, Zr, Nb, Mo, Ba, W, Pb, Bi, La, Ce, Th and the second metal oxide includes one of K, Li, Be B, Na, Mg, Al, Si, Ca, Sc, Ti, V, Cr, Mn, Fe, Co, Ni, Cu, Zn, Br, Sr, Y, Zr, Nb, Mo, Ba, W, Pb, Bi, La, Ce, Th, or a combination of these, the first metal oxide not being same as the second metal oxide; and/or
  wherein the first metal oxide includes an oxide of potassium and the second metal oxide includes an oxide of titanium, or the first metal oxide includes an oxide of tungsten or cerium and the second metal oxide includes an oxide of zirconium, titanium, silicon, vanadium, or chromium, or includes an oxide of zirconium or titanium; and/or
  wherein the content of the first metal oxide in the catalyst system is 13.0 to 30.0 wt-% calculated by weight of metal oxide relative to the total mass of the catalyst.

22. The method according to claim 10, wherein the content of the at least one ketoacid in the feedstock is at least 30.0 wt-%; and/or
  wherein the weight ratio of the at least one ketoacid content to the at least one ketoacid dimer content in the feedstock [ketoacid:ketoacid dimer] is in the range of 1:3 to 5:1.

23. The method according to claim 1, wherein the feedstock is introduced into the reactor in liquid phase; and/or
  wherein the second C—C-coupling reaction(s) are conducted at a temperature in the range of 220-260° C.; and/or
  wherein the second C—C-coupling reaction(s) are conducted at a pressure in the range of 1.0-20 bar; and/or
  wherein the second C—C-coupling reaction(s) are conducted at a weight hourly space velocity (kg feedstock/kg catalyst*h) in the range of 0.25 $h^{-1}$ to 1.25 $h^{-1}$; and/or
  wherein the feedstock includes at least one of 4-hydroxy-4-methyl-6-oxononanedioic acid, 3-acetyl-4-hydroxy-4-methylheptanedioic acid, 5-(2-methyl-5-oxotetrahydrofuran-2-yl)-4-oxopentanoic acid, (E)-4-methyl-6-oxonon-4-enedioic acid, 4-hydroxy-6-methylnonanedioic acid, (E)-6-hydroxy-4-methylnon-4-enedioic acid, (Z)-3-acetyl-4-methylhept-3-enedioic acid, 3-(3-acetyl-2-methyl-5-oxotetrahydrofuran-2-yl) propanoic acid, (Z)-3-1(1-hydroxyethyl)-4-methylhept-3-enedioic acid, and 3-(1-hydroxyethyl)-4-methylheptanedioic acid.

24. The method according to claim 12, wherein the second C—C-coupling reaction(s) are conducted at a temperature in the range of 210-300° C.

25. The method according to claim 1, wherein the ketoacid comprises pyruvic acid, oxaloacetic acid, alpha-ketoglutaric acid, acetoacetic acid, or levulinic acid.

* * * * *